(12) United States Patent
Case et al.

(10) Patent No.: US 8,057,739 B2
(45) Date of Patent: Nov. 15, 2011

(54) LIQUID PURIFICATION SYSTEM

(75) Inventors: Wayne A. Case, Portland, OR (US); Levi New, Kalamazoo, MI (US)

(73) Assignee: PulverDryer USA, Inc., Galesburg, MI (US)

( * ) Notice: Subject to any disclaimer, the term of this patent is extended or adjusted under 35 U.S.C. 154(b) by 218 days.

(21) Appl. No.: 11/243,541

(22) Filed: Oct. 5, 2005

(65) Prior Publication Data

US 2006/0051236 A1 Mar. 9, 2006

(51) Int. Cl.
*A61L 2/00* (2006.01)

(52) U.S. Cl. .................... 422/20; 422/1; 422/128

(58) Field of Classification Search .............. None
See application file for complete search history.

(56) References Cited

U.S. PATENT DOCUMENTS

| | | | |
|---|---|---|---|
| 3,255,793 A | 6/1966 | Clute | 146/1 |
| 3,699,814 A * | 10/1972 | Kaufman | 73/863.11 |
| 4,102,654 A | 7/1978 | Pellin | |
| 4,272,499 A | 6/1981 | Cason et al. | |
| 4,390,131 A | 6/1983 | Pickrel | 241/1 |
| 4,418,871 A | 12/1983 | Powell | 241/1 |
| 4,439,042 A | 3/1984 | Bertoglio | 366/154 |
| 4,848,673 A | 7/1989 | Masuda et al. | 241/5 |
| 5,242,270 A | 9/1993 | Partington et al. | 416/248 |
| 6,024,307 A | 2/2000 | Sand et al. | 241/24.1 |
| 6,289,143 B1 | 9/2001 | Berthold et al. | 385/12 |
| 6,491,242 B1 | 12/2002 | Dingee, IV et al. | 241/39 |
| 6,588,686 B2 | 7/2003 | Dingee, IV et al. | 241/5 |
| 6,722,594 B2 | 4/2004 | Graham | 241/39 |
| 7,040,557 B2 | 5/2006 | Graham et al. | |
| 7,059,550 B2 | 6/2006 | Graham et al. | |
| 2001/0042802 A1 | 11/2001 | Youds | 241/5 |
| 2003/0021720 A1 | 1/2003 | Reisfeld et al. | |
| 2003/0206796 A1 | 11/2003 | Scholten | |
| 2004/0200910 A1 | 10/2004 | Graham et al. | 241/5 |
| 2006/0051236 A1 | 3/2006 | Case et al. | |
| 2006/0097090 A1 | 5/2006 | Graham et al. | |

FOREIGN PATENT DOCUMENTS

| | | |
|---|---|---|
| DE | 197 47 628 A1 | 5/1999 |
| EP | 0 079 300 B1 | 5/1983 |
| FR | 2 311 588 | 12/1976 |
| FR | 2 661 450 A1 | 4/1990 |
| GB | 313 582 A | 12/1929 |
| GB | 591 921 A | 9/1947 |
| GB | 911 454 | 11/1962 |
| GB | 2 354 232 | 3/2001 |
| GB | 2 357 499 | 6/2001 |
| GB | 2 357 712 B | 10/2002 |

(Continued)

OTHER PUBLICATIONS

Office Action for U.S. Appl. No. 11/298,142 from USPTO mailed Sep. 13, 2007, 6 pages.

(Continued)

*Primary Examiner* — Walter Griffin
*Assistant Examiner* — Timothy Cleveland
(74) *Attorney, Agent, or Firm* — John R. Thompson; Stoel Rives LLP

(57) ABSTRACT

A liquid purification system operates an air flow generator to provide a high speed air flow. The air flow passes through a venturi and liquid introduced into the air flow passes through the venturi and is subjected to compression, heat, and shockwaves. The air flow generator may be computer controlled and automatically directed in response to sensed contaminants.

7 Claims, 4 Drawing Sheets

FOREIGN PATENT DOCUMENTS

| | | |
|---|---|---|
| JP | 01125554 | 5/1989 |
| JP | 11 160290 A | 6/1999 |
| SU | 1768242 A1 * | 10/1992 |
| WO | WO 92/12795 | 8/1992 |
| WO | 93/12884 A1 | 7/1993 |
| WO | 98/35756 | 8/1998 |
| WO | WO 99/53130 | 10/1999 |
| WO | WO 00/13799 | 3/2000 |
| WO | WO 01/03840 A1 | 1/2001 |
| WO | 01/12332 A2 | 2/2001 |
| WO | WO 02/08630 | 1/2002 |
| WO | WO 03/006166 A1 | 1/2003 |

OTHER PUBLICATIONS

Office Action for U.S. Appl. No. 11/478,900 from USPTO mailed Dec. 27, 2007, 11 pages.

* cited by examiner

LIQUID PURIFICATION SYSTEM

RELATED APPLICATIONS

This utility application claims priority to U.S. provisional patent application No. 60/616,168 filed on Oct. 5, 2004 and entitled "Liquid Purification System" and to U.S. patent application Ser. No. 10/706,240 filed on Nov. 12, 2003 and entitled "System and Method for Pulverizing and Extracting Moisture," both of which are incorporated herein by reference.

TECHNICAL FIELD

The aspects disclosed herein relate to liquid purifiers and liquid processors and, more specifically, to systems that disrupt cells and other impurities within liquid.

BRIEF DESCRIPTION OF THE DRAWINGS

A more particular description of the invention briefly described above will be rendered by reference to the appended drawings. Understanding that these drawings only provide information concerning typical embodiments of the invention and are not therefore to be considered limiting of its scope, the invention will be described and explained with additional specificity and detail through the use of the accompanying drawings, in which.

DETAILED DESCRIPTION OF PREFERRED EMBODIMENTS

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 through 4, is not intended to limit the scope of the invention, as claimed, but is merely representative of presently preferred embodiments of the invention.

Figure 1:
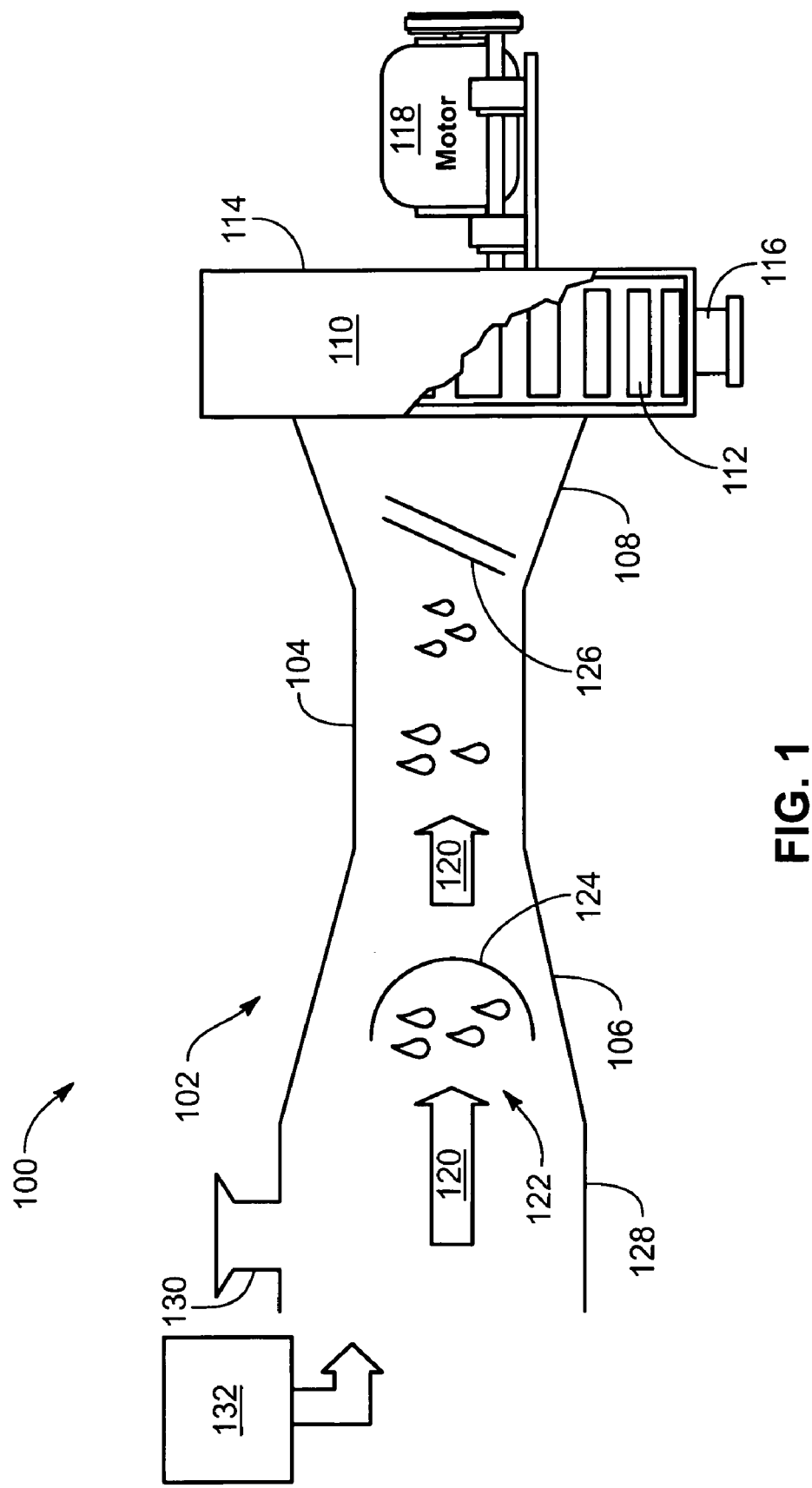
FIG. 1 is a block diagram of one embodiment of a liquid purification system of the present invention.

Referring to FIG. 1, a block diagram of a liquid purification system 100 is shown. The liquid purification system 100 includes a venturi 102 which may be embodied with a constricted portion and flared on both ends. A fluid velocity increases and the pressure decreases while passing through the constricted portion. The constricted portion is identified herein as a throat 104. The throat 104 may approximate a cylindrical shape. A converging portion 106 is coupled to one end of the throat 104, and a diverging portion 108 is coupled to the opposing end of the throat 104.

An air flow generator 110, such as an air turbine or fan, is placed in communication with the venturi 102. The air flow generator 110 may be coupled directly to the diverging portion 108 of the venturi 102. Alternatively, an intermediary component may be disposed between the venturi 102 and the air flow generator 110 provided that the component enables passage of an air flow. The air flow generator 110 pulls a stream of air through the venturi 102 and into the air flow generator 110.

The air flow generator 110 may include a rotatable turbine or fan 112 that is disposed within a housing 114. The air flow generator 110 may include an outlet 116 disposed within the housing through which an air flow may exit. A motor 118 may be coupled to the air flow generator 110 to provide rotational movement of the fan 112. As can be appreciated by one of skill in the art, the motor 118 may be embodied in various ways which are all included within the scope of the invention.

In operation, the air flow generator 110 produces an air flow 120 that may have a speed ranging from approximately 300 mph to supersonic. Liquid 122 is introduced into the air flow 120 and encounters a first shock wave 124 as the liquid 122 is introduced into the converging portion 106 of the venturi 102. The first shock wave 124 is created as the faster moving air encounters the slower moving air. As the liquid 122 proceeds into the venturi 102, the liquid 122 is subjected to extreme pressure. The liquid 122 further experiences heat generated by friction. The extreme pressure and heat creates biological cell structure reduction and destruction.

The liquid 122 further encounters a second shock wave 126 as the liquid 122 enters the diverging portion 108. The second shock wave 126 further obliterates remaining cell structure and increases liquid sterilization. Thus, liquid 122 encounters multiple forces from pressure, friction, and shockwaves that cause cell structure disruption. At greater speeds, the pressure, friction, and shockwaves are increased and greater internal molecular infraction occurs. The system 100 may be operated at speeds to generate internal forces that modify the molecular state of the liquid 122 to a gaseous state.

The liquid purification system 100 may include an inlet tube 128 that is coupled to the converging portion 106 of the venturi 102 such that the air flow 120 passes through the inlet tube 128. A hopper 130 may be coupled to the inlet tube 128. Liquid 122 may be poured into the hopper 130 to allow liquid 122 to be introduced into the air flow 120.

The liquid purification system 100 may further provide a heat source 132 to generate and introduce heat into the converging portion 106 of the venturi 102. The heat further accelerates cell destruction and sterilization of liquid 122 in the air flow 120. The heat generation may be varied based on perceived need and biological hazard. The heat source 132 may be directed into the inlet tube 128 or may feed directly into the converging portion 106.

Figure 2:
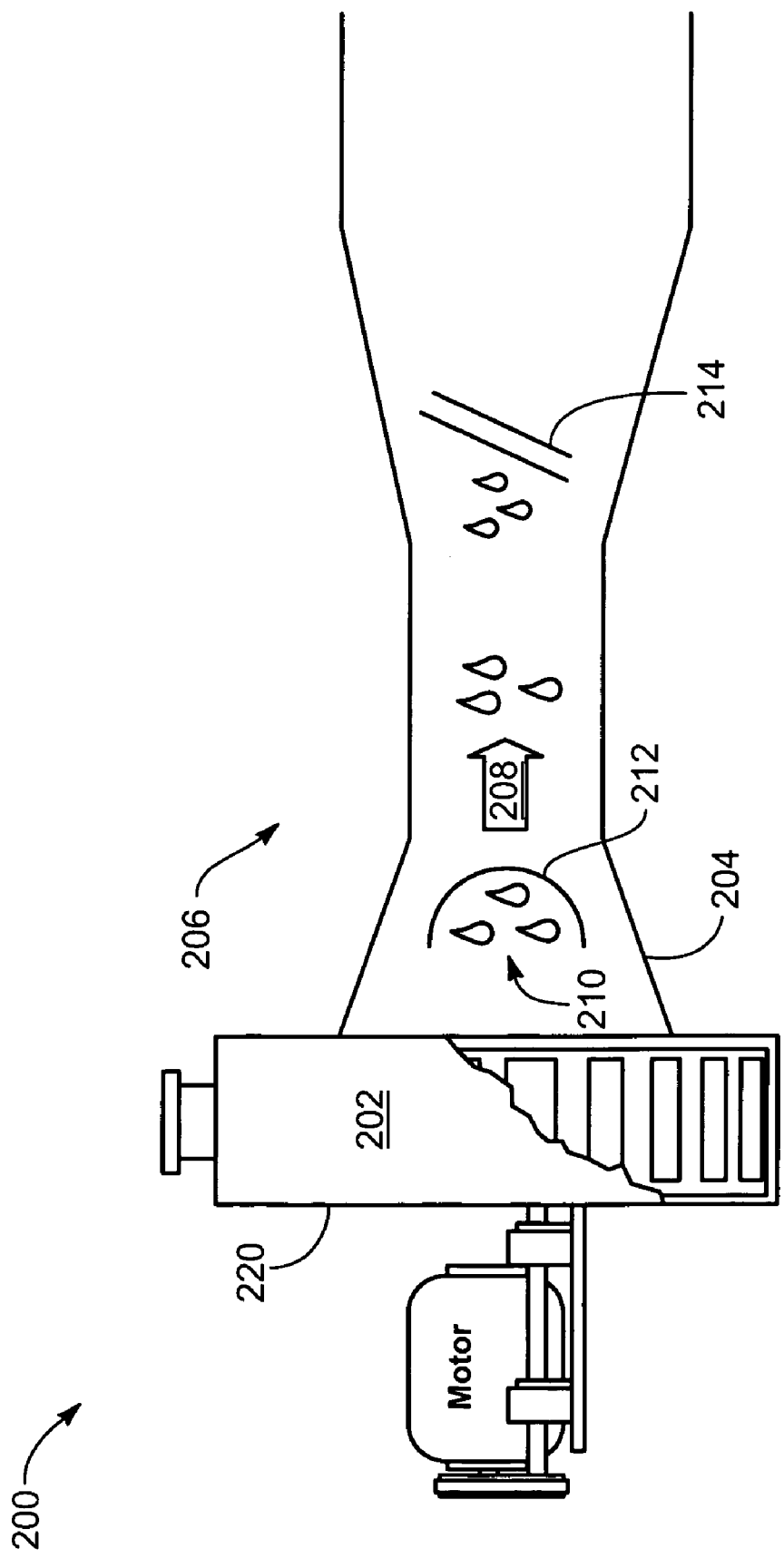
FIG. 2 is a block diagram of an alternative embodiment of a liquid purification system of the present invention.

Referring to FIG. 2, an alternative embodiment of a liquid purification system 200 is shown. The system 200 includes an air flow generator 202 that is in communication with a converging portion 204 of a venturi 206. The air flow generator 202 may be coupled directly to the converging portion 204. Alternatively, the air flow generator 202 may communicate with the venturi 206 through an intermediary component. The air flow generator 202 generates and propels an air flow 208 through the venturi 206. Liquid 210 may be introduced into the converging portion 204 through an aperture (not shown) or other access mechanism. In one embodiment, a tube may be disposed between the air flow generator 202 and the venturi 206. The tube may include a hopper or other device to permit entry into the air flow 208. As with the previous embodiment, the liquid 210 encounters first and second shock waves 212, 214 and is subjected to compression and heat.

Figure 3:
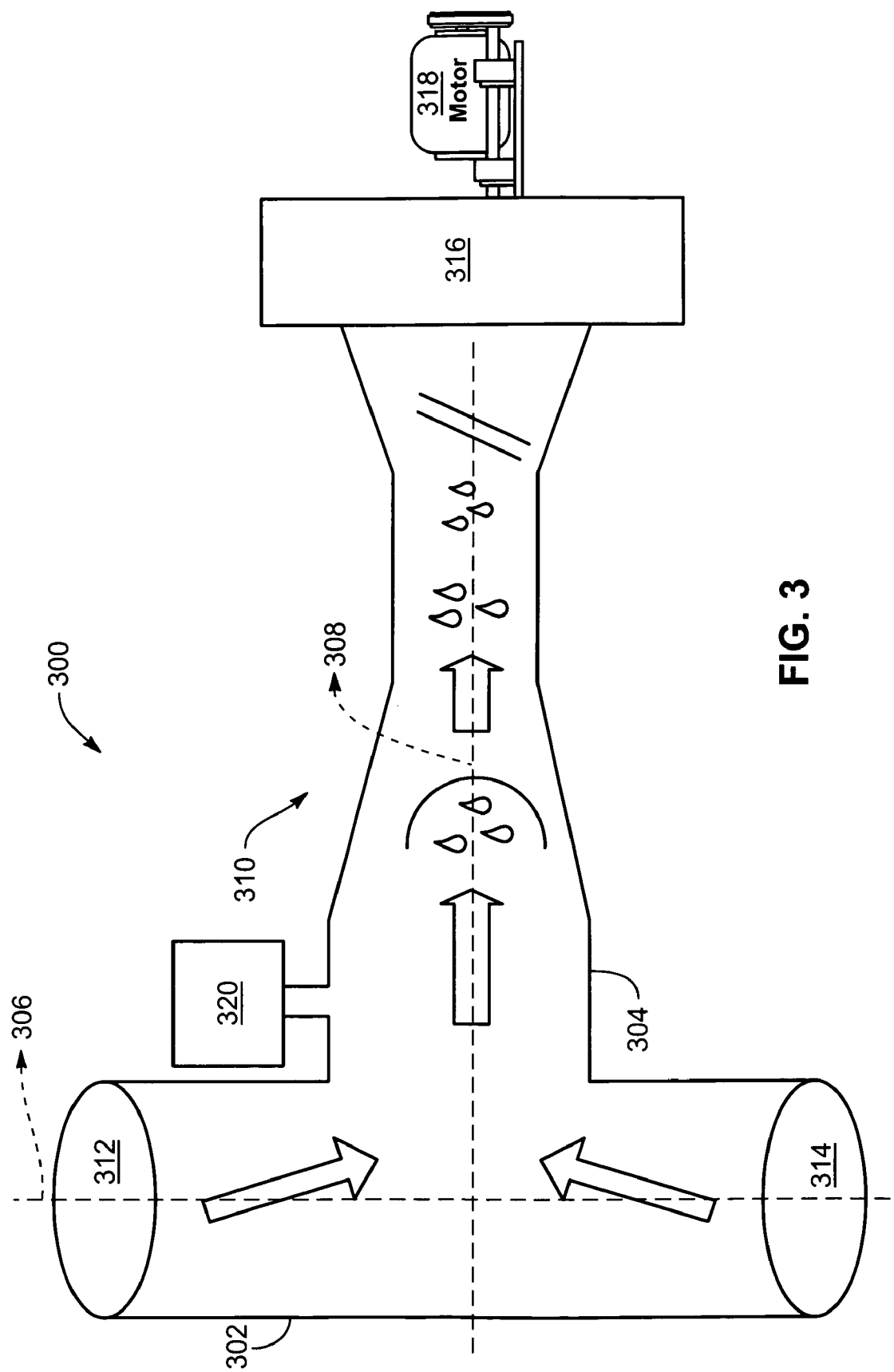
FIG. 3 is a block diagram of an alternative embodiment of a liquid purification system of the present invention.

Referring to FIG. 3, an alternative embodiment of a liquid purification system 300 is shown which includes an inlet device 302 that couples to an inlet tube 304. The inlet device 302 has a longitudinal axis 306 that may extend approximately perpendicular to a longitudinal axis 308 of a venturi 310 and inlet tube 304. The inlet device 302 may include opposing first and second apertures 312, 314 through which air passes. Liquid may be introduced into the apertures 312, 314 or into the inlet tube 304 through techniques known in the art. Valves may be disposed adjacent the apertures 312, 314 to control and direct air flow through the inlet device 302 as desired. The inlet device 302 may be coupled to an irrigation, plumping, or other fluid system to enable retrofitting. The liquid purification system 300 also includes an air flow generator 316, motor 318, and may include a heat source 320.

Cell structure resiliency varies, and the liquid purification systems disclosed herein can increase cell destructive power by increasing the RPMs of an air flow generator. The increased air flow provides for more devastating shock waves, increased friction, and dramatic changes in pressure. A heat source may input heat to further accelerate cell destruction. Thus, a liquid purification system may vary air flow velocity and heat to destroy resistant cells, such as anthrax, SARS, and other viruses.

Figure 4:
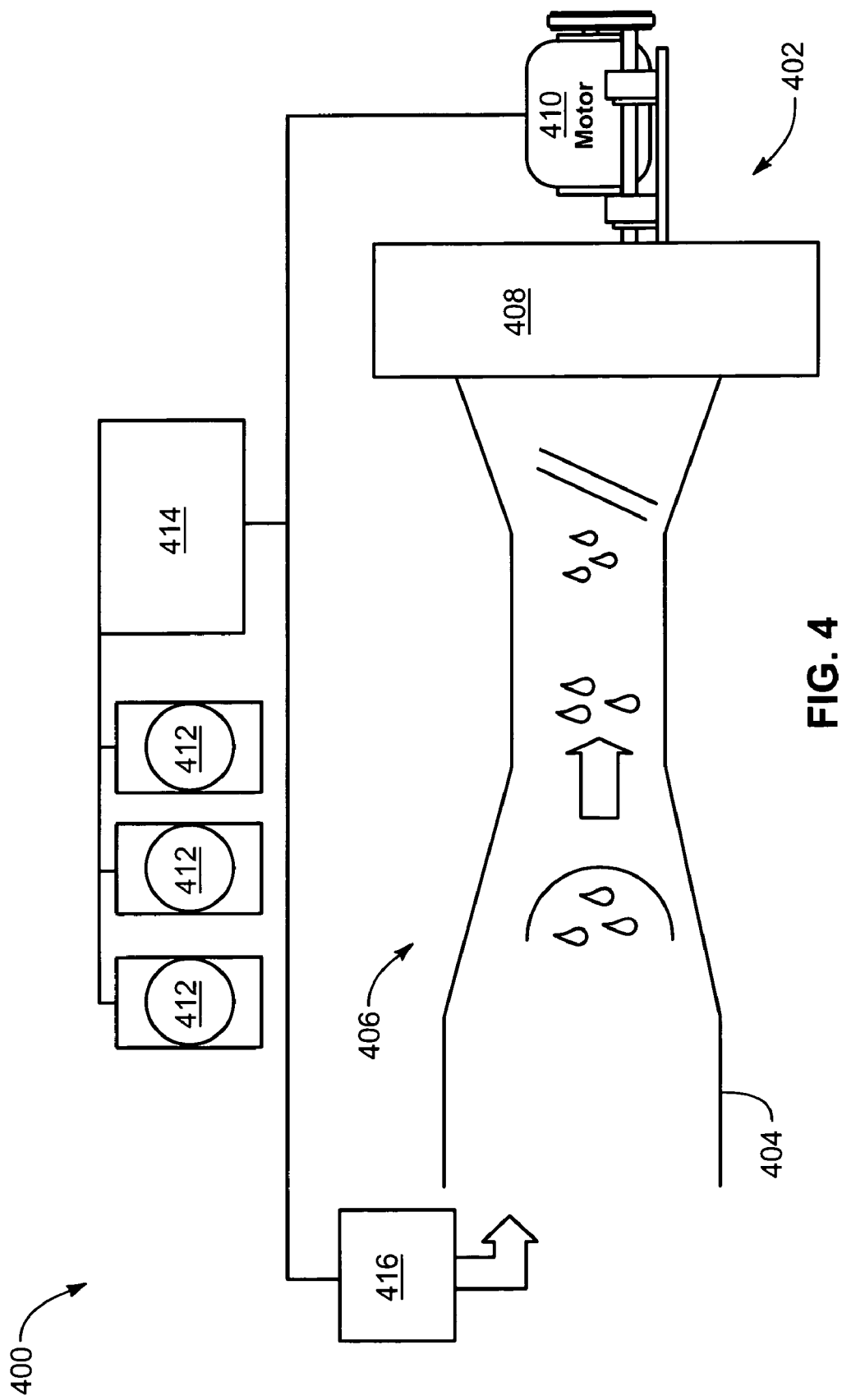
FIG. 4 is a block diagram of an alternative embodiment of a liquid purification system.

Referring to FIG. 4, a sterilization and monitoring system 400 is shown. The system 400 includes a liquid purification system 402 having an inlet tube 404, venturi 406, air flow generator 408, and motor 410. The system 400 may also include one or more sensors 412 located throughout a fluid system. The fluid system may include a water supply system for a factory, power plant, or population center. Each sensor 412 is in electrical communication with a system computer 414. A sensor 412 detects the presence of biological hazards in a fluid system.

The system computer 414 includes a processor and a memory and may also include various input devices and/or output devices. The processor may include a general purpose device, such as a 80.times.86, Pentium (mark of Intel), 680.times.0, or other "off-the-shelf" microprocessor. The processor may include a special purpose processing device, such as an ASIC, PAL, PLA, PLD, Field Programmable Gate Array, or other customized or programmable device. The memory may include static RAM, dynamic RAM, flash memory, ROM, CD-ROM, disk, tape, magnetic, optical, or other computer storage medium. The input device(s) may include a keyboard, mouse, touch screen, light pen, tablet, microphone, sensor, or other hardware with accompanying firmware and/or software. The output device(s) may include a monitor or other display, printer, speech or text synthesizer, switch, signal line, or other hardware with accompanying firmware and/or software.

The system computer 414 includes instruction code that may be embodied as hardware, software, and firmware. Suitable software to assist in implementing the invention is readily provided by those of skill in the pertinent arts using programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent arts.

The sensors 412 may communicate with the system computer 414 through a network. A network may include communications or networking software, such as the software available from Novell, Microsoft, Artisoft, and other vendors, and may operate using TCP/IP, SPX, IPX, and other protocols over twisted pair, coaxial, or optical fiber cables, telephone lines, satellites, microwave relays, modulated AC power lines, physical media transfer, and/or other data transmission "wires" known to those of skill in the art. A network may encompass smaller networks and/or be connectable to other networks through a gateway or similar mechanism.

The liquid purification system 402 may operate continuously at a reduced speed to provide a degree of liquid quality. The liquid purification system 402 may be accelerated during a hazardous situation to ensure sterilization. Although the system 400 illustrates a liquid purification system of FIG. 1, one of skill in the art will appreciate that other purification systems of the present invention may also be used.

Upon detection of a biological hazard, one or more sensors 412 signal the system computer 414 accordingly. The system computer 414 is in electrical communication with the motor 410 to drive the air flow generator 408 at sufficient speed to generate an air flow to ensure sterilization of contaminated liquid. The system computer 414 may further be in electrical communication with a heat source 416 to generate heat and advance sterilization.

One of skill in the art will appreciate that the embodiments described herein in reference to FIGS. 1-4 may be modified and remain within the scope of the invention. Thus, an inlet tube, venturi, and air flow generator may be modified in size and shape depending on design constraints and desired volumetric processing. Liquid may be introduced into an air flow through various ways known in the art including a gravitational inlet into the inlet tube, such as a hopper, injectors disposed within the inlet tube or within a hopper, and other devices known in the art. All devices for introducing liquid may include liquid volume controls by incorporating valve controls that may be operated manually or electronically.

Various types of liquids may be introduced into the liquid purification systems ranging from pure water, salt water, contaminated water, hazardous liquids, and sludge being twenty percent solid. The liquid purification systems disclosed herein are so named because not only will the systems sterilize biological cells and chemicals, but will also transform liquids to a gaseous state. Thus, disposal of contaminated or hazardous liquids may be achieved by processing the liquids through a liquid purification system. A liquid may be effectively eliminated as it is dehydrated and changed to a gaseous state.

A liquid purification system may sterilize pathogens in water that represent a significant biological threat. The contaminated water is subjected to pressure, friction, and heat sufficient to sterilize contaminants, and the resulting output is water with inert contaminants. The water may be repeatedly processed to ensure that the water is sterilized. Previously contaminated water may then be reintroduced into the environment or used for other purposes.

If desired, contaminated water may be turned into a gaseous state by operating a system at higher speeds to alter the water's molecular state. The resulting output is hydrogen and oxygen gases that may include some residual contaminants. The gases may then be filtered to remove residual contaminants. This process ensures that the contaminated water will not be reintroduced into the environment.

The liquid purification system may process liquids that include semi-solids. The liquid is converted to gas, and the solids are converted to a powder. If the resulting powder is not sufficiently dehydrated, the powder may be processed until sufficient dehydration occurs.

If desired, the systems described herein may process water at speeds to achieve a gaseous transformation and thereby function as a dehydrator or a hydrogen and/or oxygen generator. Water with the desired purity level is introduced into a system and hydrogen and oxygen vents through an output. In operation, no noticeable water residue is found within the system, and no significant water condensation occurs. Hydrogen and oxygen may be separated at the output using conventional techniques known in the art. As can be appreciated, other liquids may be transformed from a liquid to a gaseous state as desired.

A particularly advantageous feature of the system is the ability to eliminate hazardous liquid materials. Presently, numerous industries stagger under the burden of eliminating volumes of hazardous liquid materials. The present invention is capable of reducing liquid tons to handfuls of powder. With such capability, the present invention has broad application for a wide range of industries that deal with material manipulation.

One application with tremendous promise is the processing of blood and semi-solid animal parts in slaughter houses and food processing plants. In operation, blood processed by a liquid purification system is almost entirely converted into a gaseous state. This is a marked improvement over conventional disposal techniques that require transportation and the use of land fills. Processed animal organs are dehydrated and converted into a powder form. The powder may be disposed of, used for animal feed, or used for other food products.

The embodiments herein disclose a mechanical purification apparatus that is reliable and efficient to operate. With speeds approaching supersonic or greater, the liquid purification system pressurizes, heats, and applies shockwaves to liquid. A liquid purification system may be used in any number of situations where harmful cells or chemicals must be sterilized, where disposal of hazardous liquids is required, or where gas generation is desired.

The above description of illustrated embodiments of the invention is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize. These and other modifications can be made to the invention in light of the above-detailed description.

The invention claimed is:

1. A sterilization and monitoring system for detecting and destroying contaminants in a liquid, comprising:
   a plurality of sensors, each sensor to detect contaminants and generate a signal indicative of the contaminant presence in a liquid;
   a computer in electrical communication with the sensors and to receive the signal; and
   a liquid purification system including,
      a venturi, including a converging portion, a throat, and a diverging portion,
      an air flow generator in communication with the venturi to generate an air flow through the venturi, wherein contaminants in a liquid introduced into the air flow are subjected to compression and shockwaves as the liquid passes through the venturi, and
      a motor coupled to the air flow generator and in electrical communication with the computer, wherein the computer directs operation of the motor.

2. The sterilization and monitoring system of claim 1, further comprising a heat generator in communication with the venturi and wherein the computer is in electrical communication with the heat generator to direct operation of the heat generator.

3. The sterilization and monitoring system of claim 1, wherein the air flow generator directs an air flow towards the air flow generator.

4. The sterilization and monitoring system of claim 1, wherein the air flow generator directs an air flow away from the air flow generator.

5. The sterilization and monitoring system of claim 1, further comprising an inlet tube coupled to the converging portion.

6. The sterilization and monitoring system of claim 5, further comprising an inlet device coupled to the inlet tube, the inlet device having a longitudinal axis substantially perpendicular to a longitudinal axis of the inlet tube, the inlet device including opposing first and second apertures.

7. The sterilization and monitoring system of claim 1, wherein the air flow generator is coupled to the diverging portion of the venturi.

* * * * *